United States Patent
Murata

(10) Patent No.: US 6,582,659 B1
(45) Date of Patent: Jun. 24, 2003

(54) EQUIPMENT FOR CLINICAL EXAMINATION

(75) Inventor: Yasuhito Murata, Kyoto (JP)

(73) Assignee: Kyoto Daiichi Kagaku Co., Ltd., Kyoto (JP)

( * ) Notice: Subject to any disclaimer, the term of this patent is extended or adjusted under 35 U.S.C. 154(b) by 0 days.

(21) Appl. No.: 09/446,143

(22) PCT Filed: Jun. 11, 1998

(86) PCT No.: PCT/JP98/02574

§ 371 (c)(1), (2), (4) Date: Dec. 10, 1999

(87) PCT Pub. No.: WO98/57170

PCT Pub. Date: Dec. 17, 1998

(30) Foreign Application Priority Data

Jun. 12, 1997 (JP) ............................................. 9-154953

(51) Int. Cl.[7] ........................... G01N 21/75; B01L 7/00; B01L 11/00; H05B 6/40

(52) U.S. Cl. ..................... 422/64; 422/68.1; 422/82.12; 422/104; 422/284; 422/287; 422/290; 219/635; 219/647; 219/660; 219/676

(58) Field of Search .......................... 422/99–100, 102, 422/104, 63–64, 284, 285, 287, 298–299, 65–67, 300, 307, 939, 943, 78, 290, 82.12; 435/287.3, 303.1; 219/628, 630, 618, 622, 634–635, 647, 672, 676, 624, 660; 374/12–13, 208

(56) References Cited

U.S. PATENT DOCUMENTS 3,816,687 A * 6/1974 Heitner
3,856,470 A 12/1974 Cullis et al.
5,336,467 A 8/1994 Heidt et al.
5,560,888 A * 10/1996 Seto et al. ..................... 422/63

FOREIGN PATENT DOCUMENTS

| DE | 44 28 228 | 2/1996 |
| FR | 2 281 273 | 3/1976 |
| JP | 63-266292 | 11/1988 |
| JP | 2-179493 | 7/1990 |
| JP | 3-12166 | 2/1991 |
| JP | 3-506075 | 12/1991 |
| JP | 7-142160 | * 6/1995 |
| JP | 9-72912 | 3/1997 |
| JP | 11-204243 | * 7/1999 |

* cited by examiner

Primary Examiner—W. L. Walker
Assistant Examiner—Marianne Ocampo
(74) Attorney, Agent, or Firm—Merchant & Gould, P.C.

(57) ABSTRACT

A clinical test apparatus includes a reaction table (1) for placing a test piece thereon for reaction of the test piece with an analyte at a predetermined temperature to perform analysis. The clinical test apparatus includes a primary coil (3) fixed, as molded and sealed in resin, on a base facing the reverse surface of the reaction table (1) and supplied with alternating power, a secondary coil (4) mounted, as molded and sealed in resin, on the reverse surface of the reaction table (1) in facing relation to the primary coil (3) for inducing an electromotive force due to the alternating power supplied to the primary coil and a heater (5) built in the reaction table (1) for generating heat due to the electromotive force induced in the secondary coil.

6 Claims, 4 Drawing Sheets

EQUIPMENT FOR CLINICAL EXAMINATION

TECHNICAL FIELD

The present invention relates to a clinical test apparatus for performing clinical analysis based on color reaction of a test piece impregnated with an analyte. More particularly, the present invention relates to a clinical test apparatus in which the test piece undergoes reaction on a rotary reaction table at a predetermined temperature.

BACKGROUND OF THE INVENTION

This kind of clinical test apparatus is known which, in one example, comprises a reaction table for placing a urine test piece which is impregnated with urine as an analyte for reaction therewith to determine the concentration of a urine constituent on color reaction of the test piece.

This kind of clinical test apparatus mainly includes a reaction table rotated by the driving force of a stepping motor via a drive shaft, a measuring/testing section for directing light to a predetermined position on the reaction table and for determining the concentration of an urine constituent on the basis of the light reflected on the urine test piece which has undergone color reaction, and a suction device for sucking an excess of urine deposited on the urine test piece and/or the reaction table.

However, the suction device is incapable of completely removing the urine excess deposited on the urine test piece and the reaction table. As a result, the reaction table is easily contaminated with urine and therefore is likely to a become unclean. Accordingly, the reaction table should be removed from the apparatus body for the purpose of cleaning with water for example before or after the analysis of the urine test piece.

Further, for improving the accuracy of analysis in such a clinical test apparatus, it has been proposed to cause the urine test piece to react with urine at a predetermined temperature. For instance, a heater may be disposed near the reaction table to raise the temperature of the atmosphere around the reaction table, or a heat plate is provided in direct contact with the reaction table to raise the temperature from outside the reaction table.

However, in such a conventionally proposed apparatus, heat is transmitted to the reaction table from outside; i.e., from a heater disposed near the reaction table or from a heat plate disposed indirect contact with the reaction table, for example. As a result, heat cannot be efficiently transmitted to the urine test piece placed on the reaction table, and therefore, it has been difficult to analyze the urine test piece at an appropriate temperature.

It is, therefore, an object of the present invention to provide a clinical test apparatus wherein heat is transmitted from inside the reaction table to the urine test piece for analyzing the urine test piece on the reaction table at an appropriate temperature while making the reaction table removable from the apparatus body for cleaning purposes.

SUMMARY OF THE INVENTION

In accordance with the present invention, there is provided a clinical test apparatus for measuring/testing a test piece which is impregnated with an analyte and placed on a reaction table for reaction with the analyte at a predetermined temperature, the apparatus comprising: a primary coil provided at a position adjacent the reaction table and supplied with alternating power; a secondary coil provided on the reaction table in facing relation to the primary coil for inducing an electromotive force due to the alternating power supplied to the primary coil; and a heater mounted to the reaction table for generating heat due to the electromotive force induced in the secondary coil.

With the clinical test apparatus having the above structure, when AC power is supplied to the primary coil provided adjacent the reaction table, an electromotive force is induced in the secondary coil provided on the reaction table in facing relation to the primary coil due to electromagnetic induction. The heater mounted on the reaction table generates heat by utilizing the electromotive force thus induced in the secondary coil 2. Thus, the heat is directly transmitted from the heater to the test piece on the reaction table, thereby enabling reliable heat transfer to the test piece.

Accordingly, with the clinical test apparatus described above, it is possible to analyze the test piece at an appropriate temperature owing to reliable heat transfer to the test piece placed on the reaction table. Further, since the reaction table can be supplied with electrical power without any electrical contact, it is possible to remove the reaction table from the apparatus body.

In a preferred embodiment, the reaction table incorporates a temperature control means for controlling the temperature of the reaction table by controlling the power supply from the secondary coil to the heater. For instance, the temperature control means is operative to reduce the power supply from the secondary coil to the heater when the temperature of the reaction table rises above a predetermined temperature, whereas it increases the power supply when the temperature of the reaction table drops below the predetermined temperature. As a result, the heating operation of the heater is controlled in a feedback manner on the basis of the temperature of the reaction table, thereby keeping the temperature of the reaction table at a predetermined level.

Therefore, in this preferred embodiment, it is possible to maintain the temperature of the reaction table at a constant level which is appropriate for reaction of the test piece with the analyte.

In a preferred embodiment, the reaction table is centrally supported at the center by a drive shaft, and the primary coil and the secondary coil are wound around the drive shaft and spaced from each other.

With such an arrangement, when the drive shaft rotates, the reaction table supported at the center by the drive shaft also rotates. As a result, the secondary coil provided on the reaction table also rotates around the drive shaft while keeping a predetermined spacing from the primary coil. Thus, when alternating magnetic flux is generated along the drive shaft due to alternating current supplied to the primary coil, the magnetic flux also penetrates centrally through the secondary coil wound around the drive shaft. As a result, an electromotive force is properly induced in the secondary coil due to electromagnetic induction.

In a preferred embodiment, the primary coil is sealed at a position adjacent the reaction table, whereas the secondary coil is sealed on the reaction table.

With such a structure, the primary coil and the secondary coil are prevented from water penetration. Accordingly, it is possible to wash the reaction table or the nearby components with water for example without causing a trouble.

In a preferred embodiment, the reaction table is removable.

With such a structure, it is possible to keep the reaction table in its mounted position during analysis of the test piece, and to remove the same when it is out of service. Thus, the entire reaction table and the nearby components can be manually reached for cleaning, thereby facilitating washing of the reaction table and the nearby components with by water for example.

Other features and advantages of the present invention will become apparent from the detailed description given below with reference to the accompanying drawings.

BEST MODE FOR CARRYING OUT THE INVENTION

The preferred embodiments of the present invention will be described below with reference to the accompanying drawings.

Figure 1:
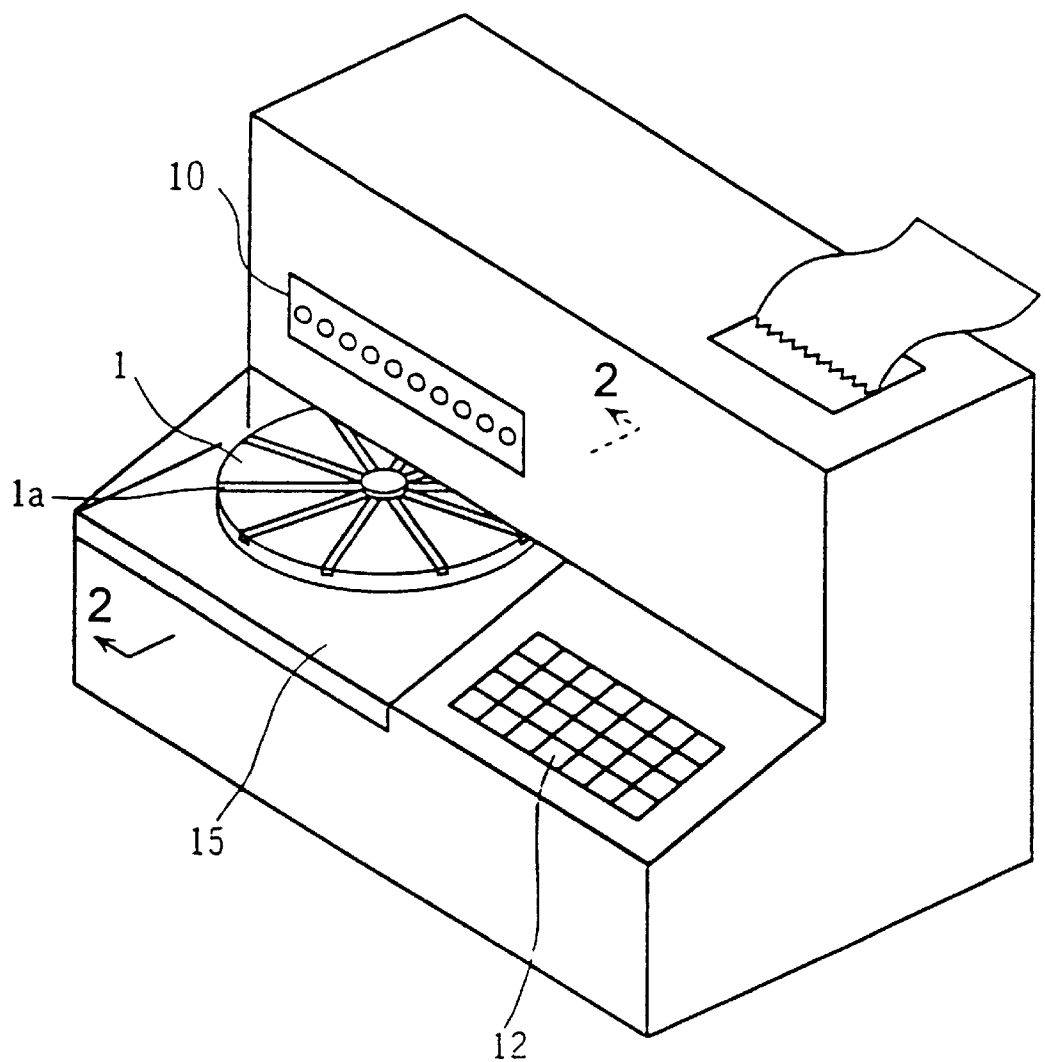
FIG. 1 is a perspective view showing the appearance of a clinical test apparatus embodying the present invention.
Figure 2:
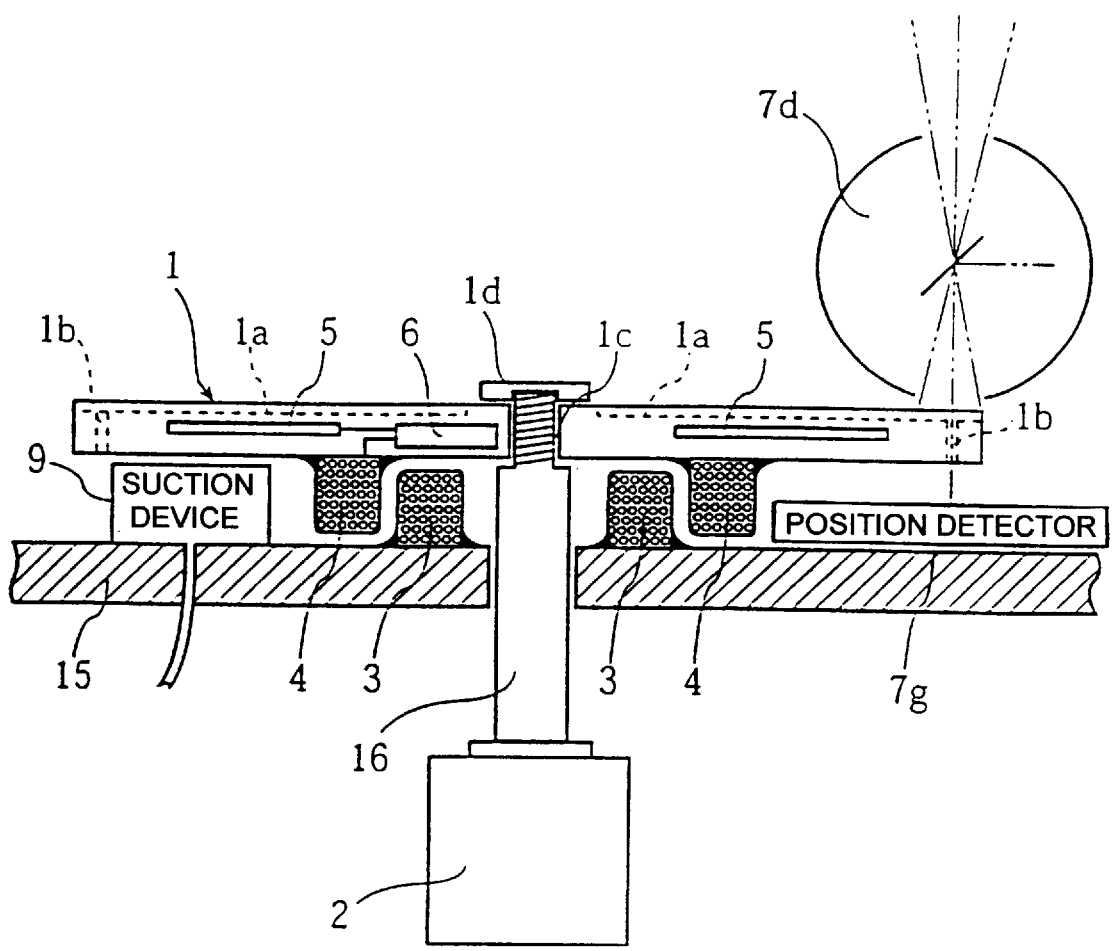
FIG. 2 is a sectional view taken along lines X—X in FIG. 1 showing the portion around the reaction table of the clinical test apparatus.
Figure 3:
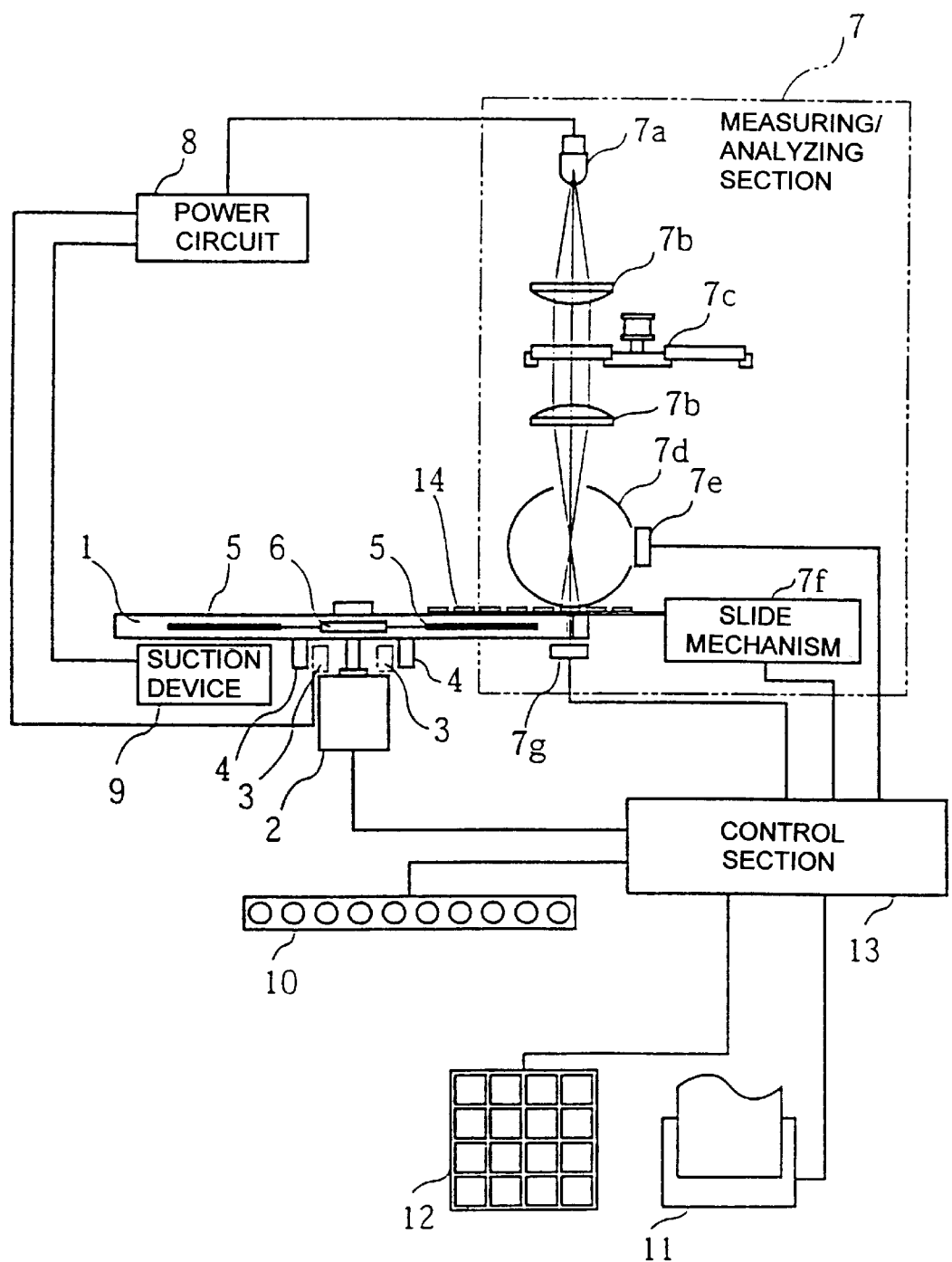
FIG. 3 is a schematic view showing the overall arrangement of the clinical test apparatus embodying the present invention.

As clearly shown in FIGS. 1 to 3, a clinical test apparatus comprises a reaction table 1, a table drive motor 2, a primary coil 3, a secondary coil 4, a heater 5, a temperature control section (temperature control means) 6, a measuring/testing section 7, a power circuit 8, a suction device 9, a timing signalizer 10, a printer 11, a keyboard 12 and a control section 13. Urine test pieces 14 each in the form of a strip may be prepared in advance for use on the reaction table 1 in the clinical test apparatus. Each of the urine test pieces carries, at predetermined portions thereof, a plurality of test pads for color reaction with urine, for example.

The apparatus includes a horizontal base 15 provided generally in the middle of the apparatus body. The reaction table 1 is disposed adjacent to the base with generally half of its surface exposed. The timing signalizer 10 is disposed on the front surface of the apparatus body above the reaction table 1. The keyboard 12 is incorporated in a control panel provided generally in the middle of the apparatus body aside of the reaction table 1. The table drive motor 2, the measuring/testing section 7, the power circuit 8, the printer 11 and the control section 13 are incorporated in the apparatus body. The primary coil 3, the secondary coil 4, the heater 5, the temperature control section 6 and the suction device 9 are disposed in or around the reaction table 1.

The reaction table 1 is formed by molding resin into a disk-like configuration. The obverse surface of the table is formed with a plurality of radially extending grooves 1a at equiangular spacing for placing the urine test pieces 14. Each of the grooves 1a is provided with a slit (not shown) for introducing an excessive amount of urea to the reverse surface of the reaction table and a round hole 1b for detecting the position of the groove 1a.

The reaction table 1 is centrally formed with a central hole 1c for inserting an end portion of a drive shaft 16. The drive shaft 16, which is disposed perpendicularly to the base 15, extends via a through-hole 15a of the base 15 and the central hole 1c, thereby transmitting a rotational torque of the table drive motor 2 to the reaction table 1. The tip end of the drive shaft 16 is fixed to the central hole 1c of the reaction table 1 by a screw 1d so that the reaction table 1 is supported by the shaft for rotation therewith at a predetermined spacing from the base 15.

As will be described later in detail, the secondary coil 4 is molded and sealed in resin for fixation to the reverse surface of the reaction table 1. The reaction table 1 incorporates, as built-in, the heater 5 and the temperature control section 6.

The table drive motor 2 comprises a stepping motor, for example. As will be described later, the table drive motor rotates the drive shaft 16 through a predetermined step angle for causing stepwise rotation of the reaction table 1 on the basis of the driving signals from the control section 13.

The primary coil 3, which is wound about the drive shaft 16 projecting from the through-hole 15a of the base 15, is hermetically molded in resin for fixation to the base 15. A current flows through the primary coil 3 due to alternating power supplied from the power circuit 8 to be described later. Thus, the primary coil 3 serves as a so-called primary induction coil of a transformer.

The secondary coil 4, which is wound about the drive shaft 16 fixed to the central hole 1c of the reaction table 1, is sealingly molded in resin for fixation to the reverse surface of the reaction table 1 in a manner such that the inner circumferential surface of the secondary coil faces the outer circumferential surface of the primary coil 3 with a predetermined spacing therebetween. Due to the current flowing through the primary coil 3, an electromotive force is induced in the secondary coil to generate a current. Thus, the secondary coil 4 serves as a so-called secondary induction coil of the transformer.

The heater 5, which is hermetically molded in resin, is built in the reaction table 1 for connection to the secondary coil 4 via the temperature control section 6 to be described later. The heater is heated due to the current supplied from the secondary coil 4 for heating the reaction table 1.

The temperature control section 6 is incorporated in the reaction table 1 by hermetically molding in resin. When the temperature of the reaction table 1 rises above a predetermined temperature, the temperature control section operates to reduce power supply from the secondary coil 4 to the heater 5. Conversely, when the temperature of the reaction table 1 drops below the predetermined temperature, the temperature control section operates to increase the power supply to the heater 5.

Figure 4:
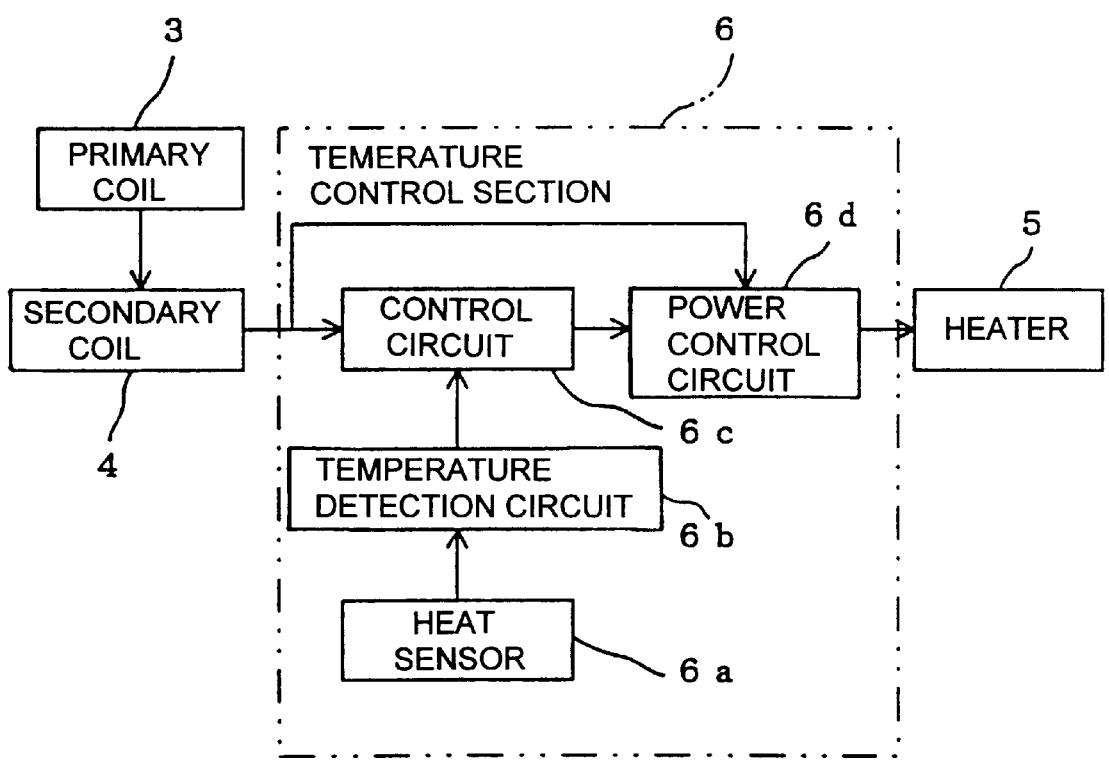
FIG. 4 is a block diagram schematically illustrating the temperature control section of the clinical test apparatus shown in FIG. 2.

Referring to FIG. 4 which is a schematic block diagram, the temperature control section 6 comprises a heat sensor 6a, a temperature detection circuit 6b, a control circuit 6c, and power control circuit 6d. The temperature control section is connected in series to the heater 5 with the secondary coil 4 serving as the power source.

With the temperature control section 6 having such an arrangement, when the heat sensor 6a detects the temperature of the reaction table 1, a signal corresponding to the detected temperature is fed from the temperature detection circuit 6b to the control circuit 6c. The control circuit 6c increases or decreases power supply from the power control circuit 6d to the heater 5, thereby increasing or decreasing the amount of heat generated by the heater 5. With the temperature control section 6 thus operating, the temperature of the reaction table 1 is kept at a constant value by setting the circuit resistance of the temperature detection circuit 6b to a predetermined value for example.

The measuring/testing section 7 mainly comprises a lamp 7a as a light source, a lens 7b, a filter 7c, an integrating sphere 7d, a detector 7e, a sliding device 7f, and a position detector 7g. The function of this section is to measure, at a predetermined measuring position on the base 15 within the apparatus body, the light reflected on the urine test piece 14 placed in each groove 1a on the reaction table 1 while the test piece slides longitudinally along the groove 1a. The detector 7e, the sliding device 7f and the position detector 7g are connected to the control section 13, which will be described later, for exchange of signals with the control section.

Specifically, when each urine test piece 14 is transferred to a predetermined measuring position by rotation of the reaction table 1, the position detector 7g senses the urine test piece through the round hole 1b provided in the groove 1a. Then, the position detector 7g transmits a position sensing signal to the control section 13 to prepare for measurement of the reflected light. Upon start of reflected light measurement, light is emitted from the lamp 7a through the lens 7b and the filter 7c to a predetermined irradiation position on the reaction table 1, whereby the light is reflected on the urine test piece 14 at the irradiation position and collected by the integrating sphere 7d for entry to the detector 7e. The detector 7e outputs a signal corresponding to the a amount of reflected light for supply to the control section 13. When the measurement at one pad of the urine test piece 14 is completed, the sliding device 7f causes the urine test piece 14 to slide along the groove 1a toward the circumference of the reaction table 1 by a pad-to-pad pitch, thereby bringing the next pad of the urine test piece 14 to the irradiation position. When the measurement is completed for all pads of the urine test piece 14, the sliding device 7f removes the urine test piece 14 from the groove 1a. The removed urine test piece 14 is then accommodated in a non-illustrated receptacle.

The power circuit 8 is connected to the primary coil 3, the lamp 7a in the measuring/testing section 7 and the suction device 9 for supplying a predetermined voltage thereto.

The suction device 9 is disposed in a space between the reverse surface of the reaction table 1 and the base 15, and mounted on the base 15 on the front side of the apparatus body. The suction device sucks, by negative pressure of a pump, an urea excess deposited on the urine test piece 14 through the slit formed at each groove 1a of the reaction table 1.

The timing signalizer 10 comprises a plurality of light-emitting elements controlled by the control section 13 to be described later. The timing signalizer provides signals representing the time for dipping the test piece in the urine analyte and the timing for placing the urine test piece 14 on the reaction table 1. In the case where the timing signalizer 10 includes ten light-emitting elements, these light-emitting elements may be turned on successively every second for example. The signalizer indicates that dipping of the test piece 14 in urine should be terminated upon lapse of eight seconds by successively turning on eight light-emitting elements. The signalizer further indicates the time in which the reaction table 1 is rotated by a predetermined number of step angles to place the urine test piece 14 at a predetermined position on the table by successively turning on the remaining two light-emitting elements.

Based on the output signals from the control section 13, the printer 11 prints, on a paper, the date and/or results of the analysis such as the concentration of an urine constituent.

The keyboard 12 is used to input various setting data such as the date.

The control section 13 comprises a microcomputer which includes a CPU, a ROM and a RAM. The control section is connected, via an interface, to the table drive motor 2, the detector 7e, the sliding device 7f, the position detector 7g, the timing signal 10, the printer 11 and the keyboard 12. The control section 13 exchanges signals with these units to control the operation thereof.

Referring to FIGS. 1 to 3, the operation of the clinical test apparatus having the above arrangement will be described.

When the clinical test apparatus is turned on by power supply, alternating current is supplied through the power circuit 8 to the primary coil 3 attached to the base 15. Due to electromagnetic induction, alternating magnetic flux is generated centrally through the primary coil 3 along the drive shaft 16.

The alternating magnetic flux thus generated in the primary coil 3 extends centrally through the secondary coil 4 attached to the reverse surface of the reaction table 1 in facing relation to the primary coil 3. As a result, current is induced in the secondary coil 4 due to electromagnetic induction.

The current induced in the secondary coil 4 is fed through the temperature control section 6 in the reaction table 1 to the heater 5 incorporated in the reaction table 1. The heater 5 is thus actuated while the amount of heat generation is controlled by the temperature control section 6.

Specifically, when the temperature of the reaction table 1 rises above a predetermined temperature suitable for reaction of the urine test piece 14, the temperature control section 6 reduces power supply from the secondary coil 4 to the heater 5. Conversely, when the temperature of the reaction table 1 drops below the predetermined temperature, the power supply is increased. Thus, the heating operation of the heater 5 is performed under feedback control on the basis of the temperature so that the reaction table 1 is maintained at a predetermined temperature suitable for reaction of the urine test piece 14.

With the temperature thus controlled for proper reaction of the test piece 14, the urine test piece 14 is placed in a respective groove 1a of the reaction table 1 for performing analysis at the measuring/testing section 7 according to light reflection.

Specifically, in accordance with the timing signals from the timing signalizer 10, the operator dips the urine test piece 14 in an analyte for a predetermined period. Then, the urine test piece 14 is placed in a respective groove 1a of the reaction table 1 which is half-exposed on the front side of the apparatus body.

When the urine test piece 14 is placed in the groove 1a, the suction device 9 provided between the reverse surface of the reaction table 1 and the base 15 sucks an urea excess through the slit.

Upon lapse of e.g. ten seconds as indicated by the signals of the timing signalizer 10, the table drive motor 2 is actuated to rotate the drive shaft 16 by a predetermined step angle. As a result, the reaction table 1 fixed to the tip end of the drive shaft 16 is rotated by that step angle to transfer the urine test piece 14 in the groove 1a to the measuring/testing section 7 within the apparatus body.

In the measuring/testing section 7, measurement is performed with respect to the light reflected on the urine test piece 14 which has been brought to that section by the rotation of the reaction table 1. When the measurement is completed, the test piece 14 in the groove 1a is removed therefrom by the sliding device 7f. Upon further rotation of the reaction table 1, the groove 1a from which the test piece 14 has been removed is rotated to the front side of the apparatus body.

The detector 7e in the measuring/testing section 7 outputs a signal corresponding to the amount of light reflected on the urine test piece 14 for supply to the control section 13. Based on this signal, the control section 13 calculates the concentration of a constituent in the urine analyte for printing out at the printer 11.

While the reaction table 1 rotates during the analysis, the secondary coil 4, which is attached to the reverse surface of the reaction table 1 in facing relation to the primary coil 3, rotates at a predetermined spacing from the primary coil 3 which is attached to the base 15. Accordingly, even when the reaction table 1 rotates, a current is induced in the secondary coil 4 due to the alternating current flowing in the primary coil 3. Further, power supply to the heater 5 is controlled by the temperature control section 6, whereby the reaction table 1 is maintained at a predetermined temperature.

Before or after the analysis of the urine test piece 14, the reaction table 1 may be removed from the drive shaft 16 by pulling out the base 15 forwardly of the apparatus body and loosening the screw 1d fixed in the central hole 1c of the reaction table 1.

The reaction table 1 thus removed from the drive shaft 16 may be washed with water for example, together with the secondary coil 4 which is molded and sealed in resin. At this time, water penetration is prevented because the heater 5, the temperature control section 6 and the secondary coil 4 attached to the reaction table 1 are molded and sealed in resin.

By removing the reaction table 1 from the drive shaft 16, the primary coil 3 attached to the base 15 in facing relation to the reverse surface of there action table 1 is exposed.

Thus, the primary coil 3 may also be washed with water for example because it is also molded and sealed in resin for preventing water penetration.

As will be understood from the above description, with such a clinical test apparatus, heat is transmitted by the heater 5 from the inside of the reaction table 1 directly to the urine test piece 14 through the reaction table 1. This enables reliable heat transfer to the urine test piece 14 placed on the reaction table 1. Accordingly, it is possible to analyze the urine test piece 14 at an appropriate temperature.

Further, since the operation of the heater 5 for transferring heat to the reaction table 1 is subjected to feedback control according to the temperature, the temperature of the reaction table 1 is adjusted to a predetermined level which is most appropriate for reaction of the urine test piece 14. Thus, it is possible to keep the temperature of the reaction table 1 constant.

Furthermore, since the primary coil 3 and the secondary coil 4 are disposed concentrically in facing relation to each other in a non-contacting manner with the drive shaft 16 located at the common center, the alternating magnetic flux generated by electromagnetic induction extends along the common center. Accordingly, it is possible to reliably transmit the electromotive force generated by electromagnetic induction to the reaction table 1 without any need for a contact.

Further, the primary coil 3 attached to the base 15 and the secondary coil 14 attached to the reverse surface of the reaction table 1 are prevented from water penetration due to resin molding. Thus, it is possible to wash the entire reaction table 1 and the nearby components, which may have been contaminated with an urea excess, with water for example.

Moreover, since the heater 5 and the temperature control section 6 are built in the reaction table 1, it is possible to transfer heat from the heater 5 directly to the reaction table 1. As a result, the heat requirement can be limited in comparison with the case where heat is supplied from outside the reaction table 1, thereby reducing power consumption at the heater 5 actuated for heating.

According to the illustrated embodiment shown in the drawings, the clinical test apparatus is used for analyzing the urine test piece 14. However, the present invention is not limited thereto but may be used as an apparatus for analyzing blood.

According to the embodiment, the temperature control section 6 incorporates a heat sensor 6a. However, the present invention is not limited by such an arrangement, and power supply to the heater 5 may be controlled by switching with a thermostat.

The drive shaft 16 may be formed of a magnetic material such as ferrite. In this case, the primary coil 3 and the secondary coil 4 wound around the drive shaft 16 provide an efficient transformer with a reduced power loss.

Further, instead of rotating the reaction table 1, the measuring/testing section 7 may be moved over the reaction table 1.

According to the embodiment, the primary coil 3 is provided on the base 15, whereas the secondary coil 4 is provided on the reverse surface of the reaction table 1 which faces the base 15. However, the present invention is not limited thereto, but the secondary coil 4 may be alternatively provided on the obverse surface of the reaction table 1 with the primary coil 3 provided adjacent the obverse surface.

What is claimed is:

1. A clinical test apparatus for measuring/testing a test piece which is impregnated with an analyte and placed on a reaction table for reaction with the analyte at a predetermined temperature, the apparatus comprising:

a base;

a reaction table supported by the base and formed by molding resin into a predetermined configuration;

a primary coil provided on the base at a position adjacent the reaction table and supplied with alternating current power;

a secondary coil provided on the reaction table in facing relation to the primary coil for generating an induced electromotive force due to the alternating current power supplied to the primary coil, the secondary coil being spaced from the primary coil and the base;

a heater mounted to the reaction table for generating heat due to the electromotive force induced in the secondary coil, wherein the heater is located within a wall thickness of the reaction table and the secondary coil is molded and sealed in the molding resin which forms the reaction table; and an electrical connection for conveying electromotive force from the secondary coil to the heater.

2. The clinical test apparatus according to claim 1, wherein the base includes a drive shaft for centrally supporting the reaction table and the primary coil and the secondary coil are wound around the drive shaft and spaced from each other.

3. The clinical test apparatus according to claim 2, further comprising a connection for permitting removal of the reaction table from the drive shaft.

4. The clinical test apparatus according to claim 1, wherein the electrical connection comprises a temperature control section for controlling a temperature of the reaction table by controlling power supply from the secondary coil to the heater.

5. The clinical test apparatus according to claim 1, wherein the primary coil is attached to the base at a position adjacent the reaction table.

6. The clinical test apparatus according to claim 1, wherein the reaction table is provided with a plurality of grooves each for receiving a test piece, and the heater is located directly below the grooves.

* * * * *